(12) United States Patent
Li (10) Patent No.: US 7,933,013 B2
(45) Date of Patent: Apr. 26, 2011

(54) DETECTION OF MATERIALS BASED ON RAMAN SCATTERING AND LASER-INDUCED FLUORESCENCE BY DEEP UV EXCITATION

(75) Inventor: Eunice X. J. Li, Arlington, VA (US)

(73) Assignee: ITT Manufacturing Enterprises, Inc., Wilimington, DE (US)

( * ) Notice: Subject to any disclaimer, the term of this patent is extended or adjusted under 35 U.S.C. 154(b) by 420 days.

(21) Appl. No.: 12/125,961

(22) Filed: May 23, 2008

(65) Prior Publication Data

US 2009/0290142 A1    Nov. 26, 2009

(51) Int. Cl.
G01J 3/44 (2006.01)
(52) U.S. Cl. ..... 356/301; 250/282; 250/288; 250/482.1; 356/73; 356/300; 356/326
(58) Field of Classification Search .......... 356/300–326, 356/51, 73; 250/282–288, 458.1
See application file for complete search history.

(56) References Cited

U.S. PATENT DOCUMENTS

| 3,850,525 | A | 11/1974 | Kaye |
| 4,689,052 | A | 8/1987 | Ogren et al. |
| 5,364,795 | A | 11/1994 | Sausa et al. |
| 5,728,584 | A | 3/1998 | Sausa et al. |
| 5,759,859 | A | 6/1998 | Sausa |
| 5,826,214 | A | 10/1998 | Lieb et al. |
| 5,835,649 | A | 11/1998 | Turner et al. |
| 5,906,946 | A | 5/1999 | Sausa et al. |
| 6,287,869 | B1 | 9/2001 | Hug et al. |
| 6,477,907 | B1 | 11/2002 | Chambers et al. |
| 6,693,944 | B1 | 2/2004 | Hug et al. |
| 7,088,435 | B2 | 8/2006 | Brestel et al. |
| 7,113,275 | B2 | 9/2006 | Gardner, Jr. et al. |
| 7,245,371 | B2 | 7/2007 | Wang et al. |
| 7,359,040 | B1 | 4/2008 | Pendell-Jones et al. |
| 7,692,775 | B2 * | 4/2010 | Treado et al. ............. 356/317 |
| 2002/0109110 | A1 | 8/2002 | Some et al. |
| 2004/0155202 | A1 | 8/2004 | Poteet et al. |
| 2006/0061762 | A1 | 3/2006 | Dwight et al. |
| 2008/0170218 | A1 * | 7/2008 | Dantus et al. ............. 356/39 |

OTHER PUBLICATIONS

R. Bombach, W. Hubschmid, A. Inauen, B. Kappeli, "Simultaneous Raman and LIF Measurements in a Catalytic Burner," Proceedings 22nd IEA Task Leaders Meeting 2000 on Energy Conservation and Emissions.

(Continued)

*Primary Examiner* — Gregory J Toatley
*Assistant Examiner* — Iyabo S Alli
(74) *Attorney, Agent, or Firm* — Edell, Shapiro & Finnan, LLC (57) ABSTRACT

A system and method are provided for detecting presence of a material of interest on a surface or in a space using spectroscopic techniques. A beam of ultraviolet light is directed to the surface or space to achieve photodissociation of a material of interest in order to produce photofragment molecules that fluoresce when excited by ultraviolet light. Raman scattering of the parent target material and laser-induced fluorescence of the daughter photofragments are collected from the surface or space that may be induced by the beam of ultraviolet light. Raman spectra and fluorescence spectra are generated from the captured Raman scattering and fluorescence. The fluorescence spectra associated with the daughter photofragment molecules and the Raman spectra of the parent target material are analyzed to determine presence of the material of interest on the surface or in the space.

20 Claims, 7 Drawing Sheets

OTHER PUBLICATIONS

S. Hong, J. Birmingham, M. Fountain, "Mesochannel Gas Sampler for Rapid Sample Collection and Concentration," Mar. 2001, pp. 1-15, Prepared for the Department of Energy Under DOE Grant No. DE-FG03-00ER83048 by MesoSystems Technology, Inc. Kennewich, Washington.

Lockheed Martin Maritime Systems & Sensors, "Biological Aerosol Warning System," Cleared for Public Domain Release DoD/00-S-0607, Dec. 1999, Aug. 2003, Manassas, VA.

General Dynamics Armament and Technical Products, "Biological Agent Warning Sensor," 2007, Charlotte, NC.

Jinian Shu, Ilana Bar, Salman Rosenwaks, "Dinitrobenzene Detection by Use of One-Color Laser Photolysis and Laser-Induced Fluorescence of Vibrationally Excited NO," Applied Optics, vol. 38, No. 21, pp. 4705-4710, Jul. 20, 1999.

N. Daugey, J. Shu, I. Bar, S. Rosenwaks, "Nitrobenzene Detection by One-Color Laser-Photolysis/Laser-Induced Fluorescence of NO (v'=0-3)," Applied Spectroscopy, vol. 53, No. 1, pp. 57-64, 1999.

Gary M. Boudreaux, Tracy S. Miller, Amanda J. Kunefke, Jagdish P. Singh, Fang-Yu Yueh, David L. Monts, "Development of a Photofragmentation Laser-Induced-Fluorescence Laser Sensor For Detection of 2, 4, 6-Trinitrotoluene in Soil and Groundwater," Applied Optics, vol. 38, No. 9, pp. 1411-1417, Mar. 20, 1999.

M. Gaft, L. Nagli, "Standoff Laser Based Spectroscopy for Explosives Detection," Proc. of SPIE vol. 6739, pp. 1-13, 2007.

Dov Heflinger, Talya Arusi-Parpar, Yosef Ron, Raphael Lavi, "Application of a Unique Scheme for Remote Detection of Explosives," Optics Communications, pp. 327-331, Apr. 1, 2002.

O. Johansson, J. Bood, M. Alden, U. Lindblad, "Detection of Hydrogen Peroxide Using Photofragmentation Laser-Induced Fluorescence," Applied Spectroscopy, vol. 62, No. 1, pp. 66-72, Nov. 1, 2008.

Talya Arusi-Parpar, Dov Heflinger, Raphael Lavi, "Photodissociation Followed by Laser-Induced Fluorescence at Atmospheric Pressure and 24 C: A Unique Scheme for Remote Detection of Explosives," Applied Optics, vol. 40, No. 36, pp. 6677-6681, Dec. 20, 2001.

Carol C. Phifer, Randal L. Schmitt, Lawrence R. Thorne, Philip Hargis, Jr., John E. Parmeter, "Studies of the Laser-Induced Fluorescence of Explosives and Explosive Compositions," Sandia Report, Sandia National Laboratories, pp. 1-70, Oct. 2006.

Rosario C. Sausa, Vaidhianat Swayambunathan, Grubax Singh, "Detection of Energetic Materials by Laser Photofragmentation/Fragment Detection and Pyrolysis/Laser-Induced Fluorescence," Army Research Laboratory, Feb. 2001.

Rosario C. Sausa, George W. Lemire, Josef B. Simeonsson, "Sensitive Detection of Gas-Phase Nitro-Containing Energetic Materials Employing 226-nm Radiation," Army Research Laboratory, Jul. 1993.

J. Shu, I. Bar, S. Rosenwaks, "NO and PO Photofragments as Trace Analyte Indicators of Nitrocompounds and Organophosphonates," Applied Physics B, pp. 665-672, 2000.

Dongdong Wu, Jagdish P. Singh, Fang Y. Yueh, David L. Monts, "2,4,6-Trinitrotoluene Detection by Laser-Photofragmentation-Laser-Induced Fluorescence," Applied Optics, vol. 35, No. 21, pp. 3998-4003, Jul. 20, 1996.

C. M. Wynn, S. Palmacci, R. R. Kunz, J. J. Zayhowski, B. Edwards, M. Rothschild, "Experimental Demonstration of Remote Optical Detection of Trace Explosives," Proc. of SPIE vol. 6954, pp. 1-8, 2008.

Extended Search Report in counterpart European Application No. 09159071, dated Oct. 9, 2009.

G. W. Lemire et al., "Monitoring of Vapor-Phase Nitro Compounds Using 226-nm Radiation: Fragmentation with Subsequent NO Resonance-Enhanced Multiphoton Ionization Detection," Analytical Chemistry, vol. 65, Mar. 1, 1993, pp. 529-533, XP002549548.

* cited by examiner

DETECTION OF MATERIALS BASED ON RAMAN SCATTERING AND LASER-INDUCED FLUORESCENCE BY DEEP UV EXCITATION

BACKGROUND

There is a strong demand for systems or sensors that can detect the presence of hazardous materials, such as explosive materials, and in particular systems with high sensitivity and specificity, as well as the potential for standoff detection. Primary, secondary and tertiary explosives make up the three classes of high explosive materials, each having decreasing sensitivity to shock, friction, and heat. Peroxide-based explosives (e.g., acetone peroxides) are one of the main constituents of primary explosives, while nitro-based explosives make up the majority of secondary explosives (e.g., trinitrotoluene (TNT), cyclotrimethylenetrinitramine (RDX), pentrite (PETN)), and tertiary explosives (e.g., ammonium nitrate/fuel oil (ANFO)).

Raman spectroscopic techniques have been shown to provide high specificity in the identification of compounds. However, detection of selective high explosive materials using Raman-based sensors has limited sensitivity due to the weak Raman scattering, particularly when explosive materials are present in low concentrations, such as in the vapor phase (exemplified by high-vapor pressure peroxide-based species). On the other hand, fluorescence detection techniques are highly sensitive, typically several orders of magnitude more sensitive than Raman techniques, by comparison.

Direct detection of explosives using native fluorescence of the target substance is challenging because the fluorescence spectra are typically broad and structureless/featureless. Selective photofragments from photodissociation of explosive materials have strong fluorescence that produces structured or feature-evident spectra. Nitric oxide (NO) is a characteristic photofragment of nitro-based explosive materials when irradiated with ultraviolet (UV) light. Specifically, absorption by NO via its various A-X (v',v") bands, e.g. (0,0), (1,1), (2,2), and (0,2) transitions near 226, 224, 222, and 248 nm, results in discrete laser-induced fluorescence (LIF) emissions.

In the case of peroxide-based materials, hydroxyl radical (OH) may be the ultimate photofragment. Similarly, absorption by OH via its various A-X (v',v") bands, e.g. (1,0), (0,0), (1,1), (2,0) transitions near 282, 309, 315, 262 nm, results in discrete LIF emissions. The unique fluorescence spectral fingerprint of NO or OH can serve as a high-confidence indicator for nitro-based or peroxide-based materials, respectively, with detection sensitivities higher than the Raman signatures of their respective parent target molecules. The discrete structures in the molecular fingerprints of NO and OH are characteristic of diatomic molecules and yield distinctive fluorescence spectra in contrast to broad fluorescence profiles of larger molecules that have multiple pathways of energy disposal for populations at the excited energy levels.

There is an opportunity to exploit the unique fluorescence spectra of certain daughter photofragment molecules of a target material in order to detect the presence of the target material based on captured Raman spectra and fluorescence spectra.

SUMMARY

Briefly, a system and method are provided for detecting presence of a material of interest on a surface or in a space using spectroscopic techniques. A beam of ultraviolet light is directed to the surface or space to photodissociate a material of interest in order to produce daughter photofragment molecules that emit fluorescence when excited by ultraviolet light. Raman scattering of the parent target molecules and laser-induced fluorescence of the daughter fragments are collected from the surface or space that may be induced by the beam of ultraviolet light. Raman spectra and fluorescence spectra are generated from the captured Raman scattering and fluorescence. The fluorescence spectra associated with the daughter photofragment molecules and the Raman spectra of the parent target molecules are analyzed to determine the presence of the material of interest on the surface or in the space.

DETAILED DESCRIPTION

Techniques are provided herein to exploit the combined information obtained from the laser-induced fluorescence (LIF) spectra of daughter photofragment molecules and the Raman signatures of their respective parent targets to achieve both sensitivity and specificity in the identification of the target species. Thus, the techniques involve the simultaneous interrogation of two physical phenomena: 1) Raman scattering of the target species, and 2) LIF of the daughter photofragment (PF) species generated by photodissociation of the target species. The strength of the LIF signals and the relatively low laser fluence required of the interrogation source boost the potential for fast point detection at standoff distances compared to other detection techniques currently available.

Figure 1:
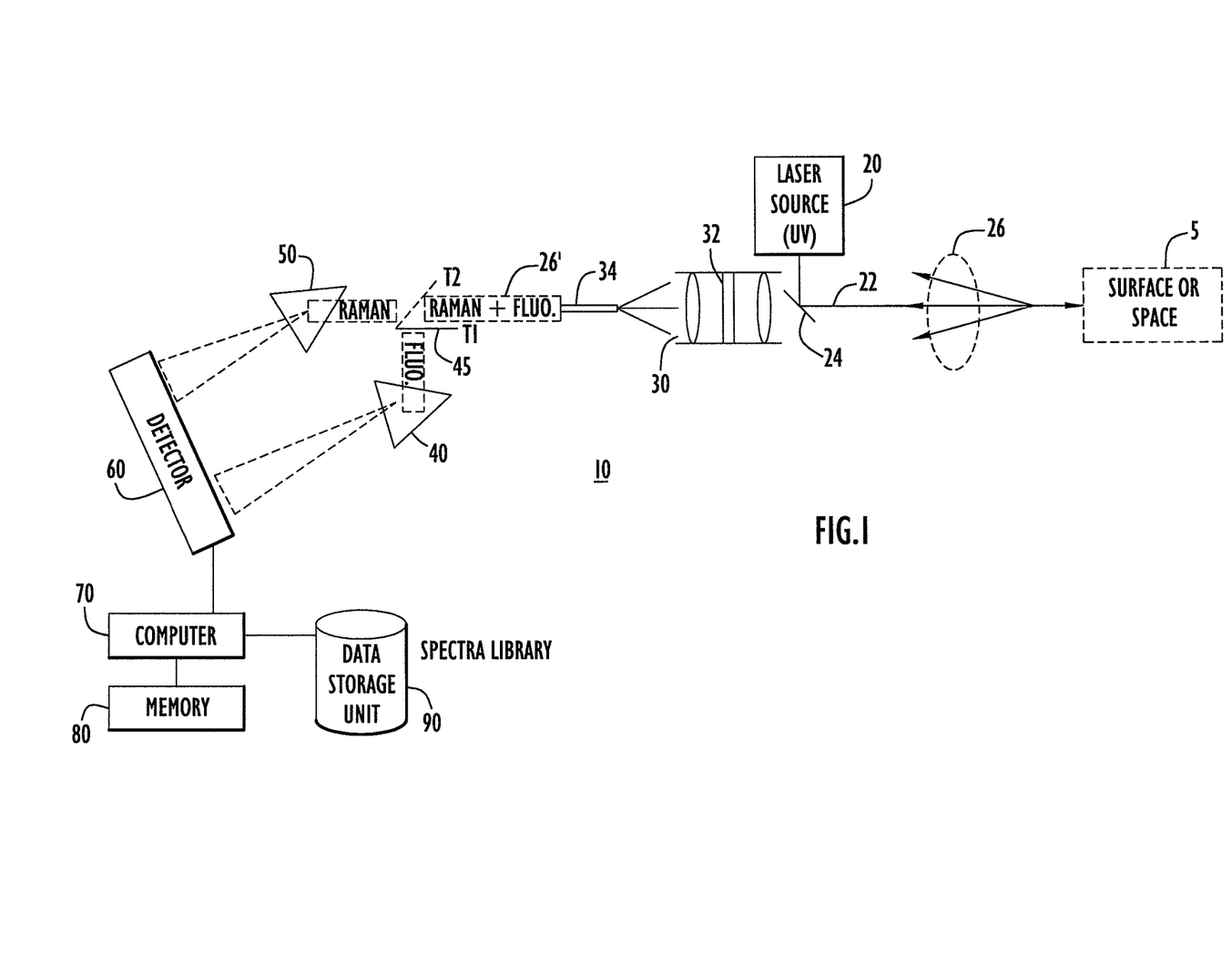
FIG. 1 is one example of a block diagram of a system for detecting the presence of a material of interest using Raman scattering and photofragmentation laser-induced fluorescence.

Referring first to FIG. 1, a block diagram of one example of a detection system 10 is shown. The system 10 comprises a laser source 20, collection optics subsystem 30 including a filter 32, first and second light dispersive elements 40 and 50, a detector 60 and a computer 70. The computer 70 may include or access separately memory 80 and a data storage unit 90 containing a library of spectra data. The system 10 may be used to detect the presence of a material of interest on a surface or within a space shown at reference numeral 5. As one example, the system may be configured to detect explosive materials as described in detail hereinafter. However, the system 10 may also be configured to detect other types of substances that are not explosive materials.

The laser source 20 is configured or adapted to produce a beam 22 of ultraviolet (UV) light at a wavelength that will induce Raman scattering as well as photofragmentation of certain molecules. For example, the laser source 20 may be a type that produces a laser beam of UV light at 222 nm, 224 nm, 226 nm, or 248 nm. An optical element 24 may be provided to direct the beam 22 to the surface or space 5.

The collection optics subsystem 30 captures the induced Raman scattering and fluorescence emissions shown at reference numeral 26 from the surface or space 5. The filter 32 eliminates from the captured Raman scattering and fluorescence emissions any energy associated with the beam from the laser source 20. While FIG. 1 shows that the laser source 20 is positioned offset from the collection optics subsystem, it is also possible that the laser source 20 is positioned directly in front of the collection optics subsystem 30.

The collection optics subsystem 30 couples the captured Raman scattering and LIF emissions 26 via an optical fiber 34 to each of the light dispersive elements 40 and 50. FIG. 1 shows that the filter 32 is positioned within the collection optics subsystem 30, but the filter 32 may also be positioned downstream of the collection optics subsystem 30 at the distal end of the optical fiber 34. There is an optical element 45 that is configured to direct the collected and filtered scattering and emissions 26' to one of the dispersive elements at a first time instant T1 (e.g., to dispersive element 50) and thereafter at time T2 to direct to the other of the dispersive elements (e.g., to dispersive element 40). Accordingly, one of the light dispersive elements 40 and 50 is used to disperse the Raman scattering and the other is used to disperse the fluorescence. For example, dispersive element 40 disperses the fluorescence and dispersive element 50 disperses the Raman scattering. In this case, the dispersive element 40 may comprise a diffraction grating that spans a range of approximately 40 nm, and the dispersive element 50 may comprise a diffraction grating that spans approximately 20 nm.

The dispersive element 40 directs the dispersed fluorescence to the detector 60 and the dispersive element 50 directs the dispersed Raman scattering to the detector 60. The detector 60 generates Raman spectra from the dispersed Raman scattering and fluorescence spectra from the dispersed fluorescence.

The computer 70 analyzes the Raman spectra and the fluorescence spectra by executing one or more software programs stored in the memory 80 to compare the Raman spectra and fluorescence spectra against the library of spectra data stored in the data storage unit 90. More generally, the functions of the computer 70 to analyze the Raman spectra and fluorescence spectra may be implemented by logic encoded in one or more tangible media (e.g., embedded logic such as an application specific integrated circuit, digital signal processor firmware instructions, software that is executed by a processor, etc.).

Figure 2:
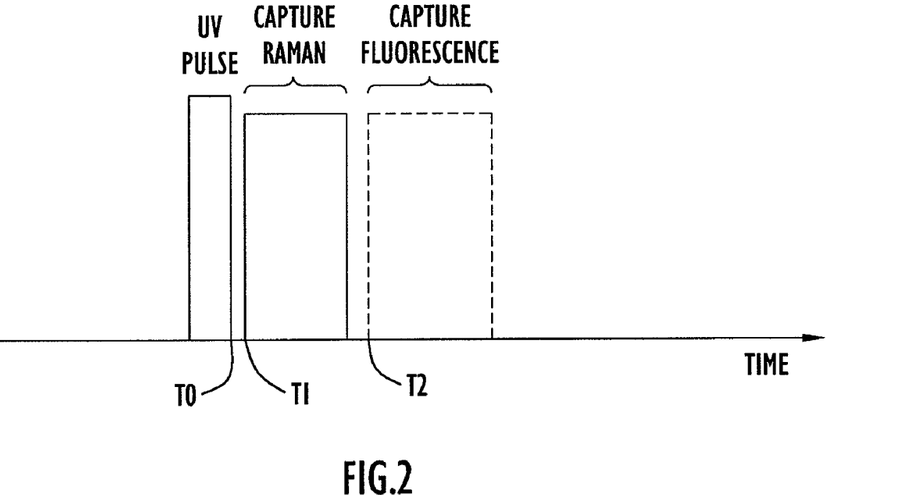
FIG. 2 is an example of a timing diagram showing capture of Raman scattering of the target materials and the laser-induced fluorescence of the daughter photofragment molecules.

Reference is now made to FIG. 2 with continued reference to FIG. 1. In one embodiment, the computer 70 is configured to control the dispersive elements 40 and 50, the optical element 45, and the detector 60 so that there is a time delay between capturing of the Raman scattering and capturing of the fluorescence. This is an example of one technique to avoid interference between the captured Raman scattering and the captured fluorescence. After conclusion of the pulse of the UV beam shown at time T0, the computer 70 controls the optical element 45 so that Raman scattering is captured beginning at time T1. Time T1 is shown to be some time interval after T0, but it should be understood that it may be nearly instantaneous with conclusion of the pulse at time T0. Some period of time after T1, the computer 70 controls the optical element 45 so that the fluorescence spectrum is captured beginning at time T2. There are other applications and examples of the techniques described herein in which there is not a sufficient delay between the production of the Raman spectra and the fluorescence spectra, examples of which are described hereinafter. In those cases, the Raman spectra and fluorescence spectra are produced substantially simultaneously. Further techniques are described herein where non-overlapping (in wavelength or wavenumber space) portions of each of the entire "window" of the Raman spectra and fluorescence spectra are analyzed to detect a target material of interest.

Figure 3:
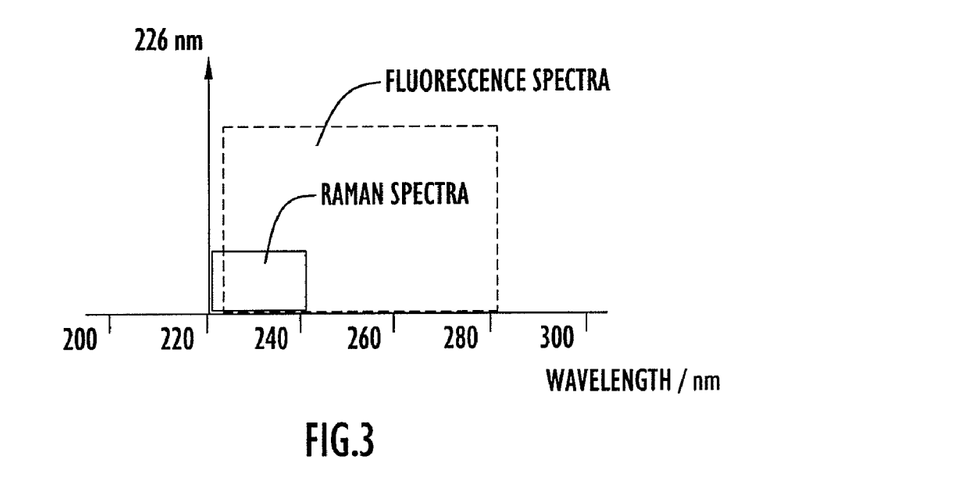
FIG. 3 is one example of a plot showing how the Raman spectra and photofragmentation laser-induced fluorescence spectra may overlap in wavelength.

FIG. 3 shows that the Raman spectra and the fluorescence spectra overlap to some extent, and in particular that the fluorescence spectrum occupies a much larger wavelength region than the Raman spectra. Furthermore, minimal fluorescence interference from the parent target molecules is expected given the characteristic low fluorescence signal from nitro-based explosive materials.

Figure 4:
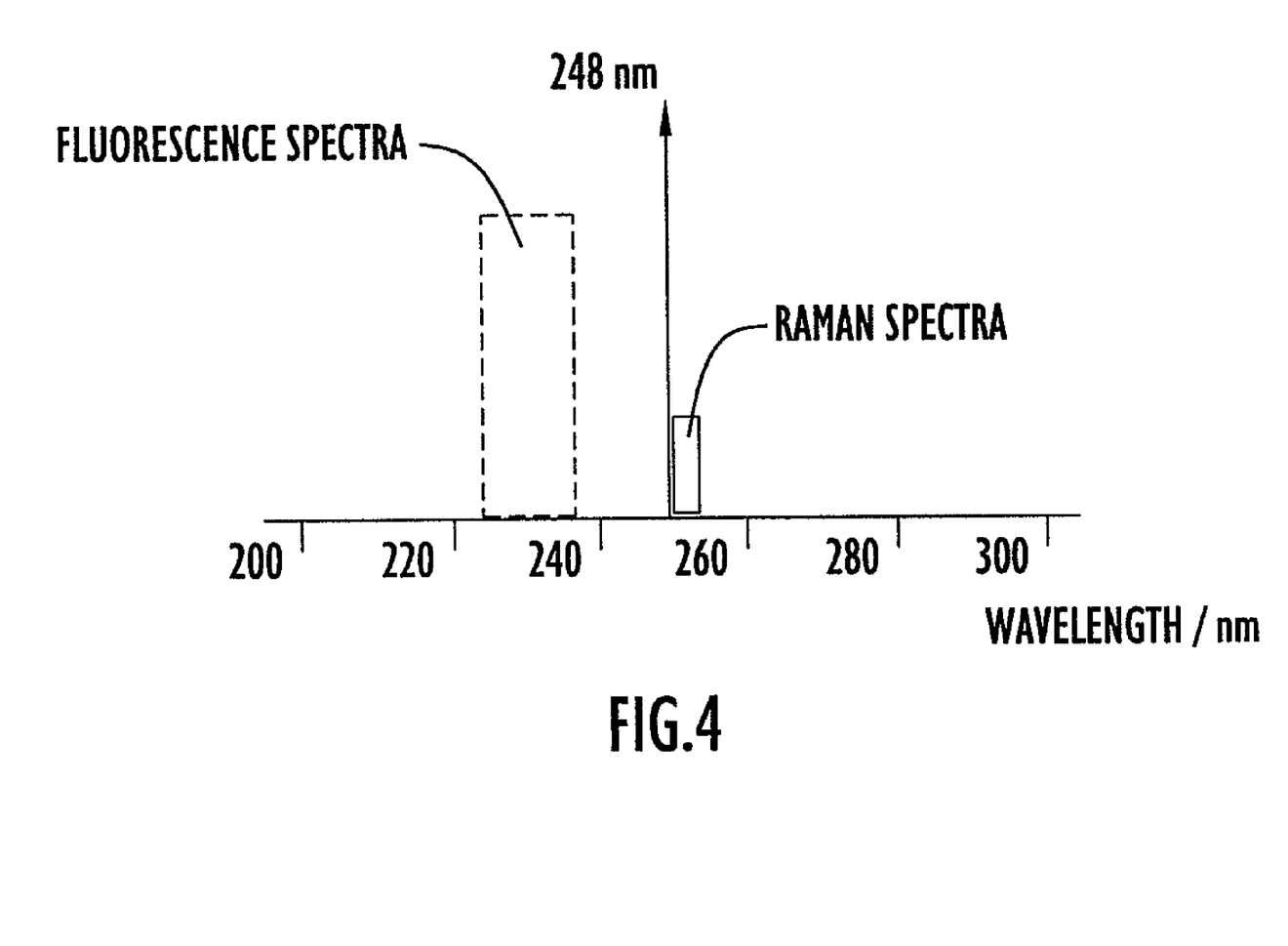
FIG. 4 is another example of a plot showing that the Raman spectra and photofragmentation laser-induced fluorescence spectra may not overlap in wavelength.

FIG. 4 shows another example in which the Raman spectra and the fluorescence spectra do not overlap.

The combined Raman spectra and photofragmentation laser-induced fluorescence (PF-LIF) techniques described herein exploits an advantage in detecting fluorescence of daughter photofragment molecules as opposed to (directly) detecting fluorescence of the parent target molecules associated with a material of interest. Direct detection of explosive materials using native fluorescence of the parent molecules is challenging because the signatures are typically broad and featureless. In the case of a nitro-based explosive material, photons in the UV laser beam photodissociate the target molecules, generating nitrogen dioxide ($NO_2$) and other fragments. Subsequent absorption of the same color photon by $NO_2$ results in predissociation of the molecule, generating nitric oxide (NO) and oxygen atom. The NO fragment can be probed via LIF, in which absorption of (subsequent or other) photons in the UV laser beam pulse by NO induces a resonance transition, promoting the ground state NO population to an excited energy state; when NO relaxes down to the ground state, fluorescence is emitted, providing a unique spectral fingerprint. Detection of PF-LIF of the NO molecules benefits from the strong UV absorption characteristic of nitro-base explosives and the requirement of minimal UV photon energy input (mJ or even µJ) to achieve strong fluorescence signals from the desired photofragments. The strength of the LIF signals provides utility in a standoff detection platform. The need for a precisely focused laser (which would limit the coverage area of the beam) is alleviated thereby enabling fast scanning over a large area. The quantity and/or concentration of explosive materials detected may also be inferred from the fluorescence intensity of the photofragments.

The laser source 20 may be controlled to use the same color (wavelength) of light (photons) to both facilitate photodissociation as well as inducing LIF of the photofragments. There are also applications in which a different color/wavelength is used for LIF than that used for photofragmentation, i.e., a pulse of light at a first wavelength to achieve photodissociation and a pulse of light of a second wavelength to induce the fluorescence.

Figure 5:
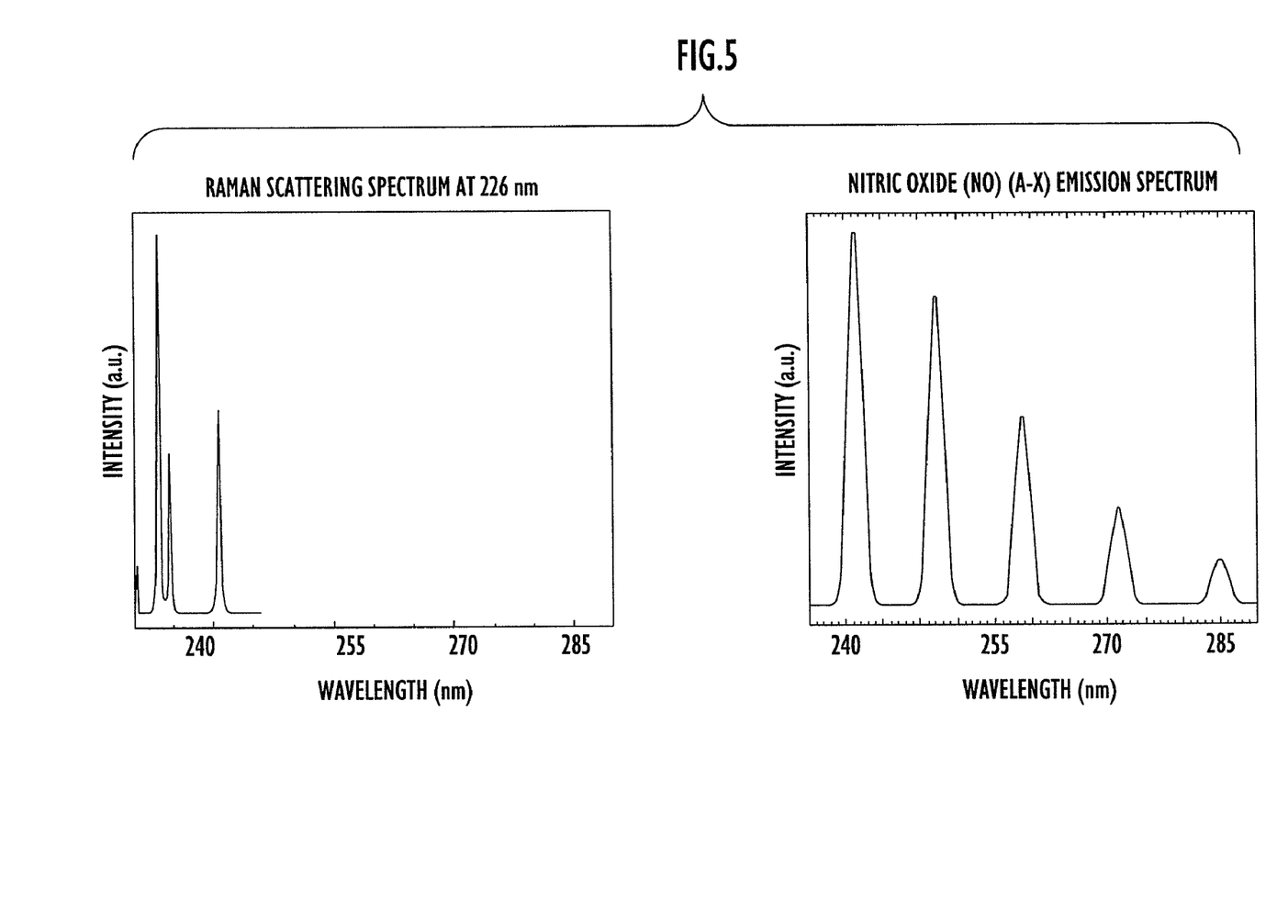
FIG. 5 illustrates examples of plots for a photofragmentation laser-induced fluorescence spectrum and a Raman spectrum according to examples where the material of interest is a nitro-based explosive material, and a detector configuration similar to that shown in FIG. 1 is used.

FIG. 5 shows examples of plots for fluorescence spectra and Raman scattering spectra that would likely result from interrogation of a surface or space in which a nitro-based explosive material is present. In particular, FIG. 5 illustrates plots that would be expected from a detector configuration of FIG. 1 that uses separate dispersive elements and detectors for Raman and LIF. The plot on the left is a plot of Raman scattering spectra of the target material, and the plot on the right is a plot of the fluorescence spectra of nitric oxide (NO) that results from PF-LIF. The fluorescence spectra plots show that there are distinctive features in the fluorescence spectra for NO. Recognizing these distinctive features in the fluorescence spectra together with other distinctive features in the Raman spectra indicative of the target molecules allows for accurate detection of certain materials of interest. In this detection example, the photofragment species have no "memory" of the parent target molecules. The PF-LIF spectra would look the same regardless of the origin of these photofragments. Therefore, detecting the PF-LIF alone does not necessarily reveal the identity of the parent molecules. It only indicates that the parent target molecules contain such photofragments. But the Raman spectra will give definite identification of the parent target molecules. That is why, in the configuration described here, the PF-LIF is complementary to Raman, and can be used as an indicator/trigger of the presence of the target materials.

In addition to nitro-based materials such as the secondary and tertiary explosives, the Raman/PF-LIF technique described herein can be applied to other booster nitrates used in the detonation of explosive materials. It can also apply to the detection of high vapor pressure peroxide-based materials, e.g. hydrogen peroxide (HOOH). Peroxide-based materials are unstable due to the weak bond strength between the bonding oxygen atoms. Absorption of UV photons (typically at wavelength <300 nm) leads to dissociation of HOOH, generating OH fragments. Subsequently, the resulting OH fragments can undergoes resonance transitions via its A-X (1,0), (0,0), (1,1), (2,0) transitions near 282, 309, 315, 262 nm, and its LIF associated with different energy levels can be collected, thereby lending feature-full fluorescence emission spectra. This LIF fingerprint of OH daughter fragments can serve as an indicator for the presence of the molecules from which OH is generated, HOOH in this case. If the same wavelength is used for dissociation of the parent HOON molecules, then a single color photon (or a single laser line) can be use for both the PF and LIF steps, like that in the case of nitro-based materials. However, the wavelength optimal for photofragmentation may be different then that needed to induce LIF of the OH photofragments. Therefore, multiple wavelengths may be use to achieve the PF-LIF process, and the Raman spectra obtained at multiple wavelengths would also provide addition information on the parent molecules as well.

The Raman/PF-LIF technique described herein can be applied to other peroxide-based materials with higher structural complexities, such as some of the primary explosives (e.g., acetone peroxides), that have peroxide bonds as the backbone of their molecular structures. In some cases, OH fragments may be generated as a direct result of UV photodissociation (at photon energy specific for each target material). In other cases, it is likely that subsequent decomposition of photofragments following photolysis of the target materials, perhaps in the presence of proton-rich species (e.g. water, acids), may be necessary to produce HOOH molecules as an intermediate reaction product, and from which OH fragments are then generated and its LIF detected as described above.

Furthermore, the Raman/PF-LIF technique described herein can be applied to chemically stable species, such as nitric acid ($HNO_3$). $HNO_3$ is widely used as a precursor for OH radicals. Although peroxide bond is absent in the molecular structure of $HNO_3$, OH radicals are readily generated upon UV photolysis of $HNO_3$ (typically at wavelengths <350 nm). Additionally, nitrogen dioxides ($NO_2$) are generated, a photolysis product complementary to OH radicals. $NO_2$ and/or its subsequent photofragment, NO, can be probed using the techniques described herein.

In general, the Raman/PF-LIF technique described herein may be employed to detect molecules/compounds (of explosive materials or any material) that can generate characteristic photofragments which have unique and distinctive fluorescence emission spectra. For example, diatomic molecules have feature-full (distinctive) fluorescence emission spectra.

Figure 6:
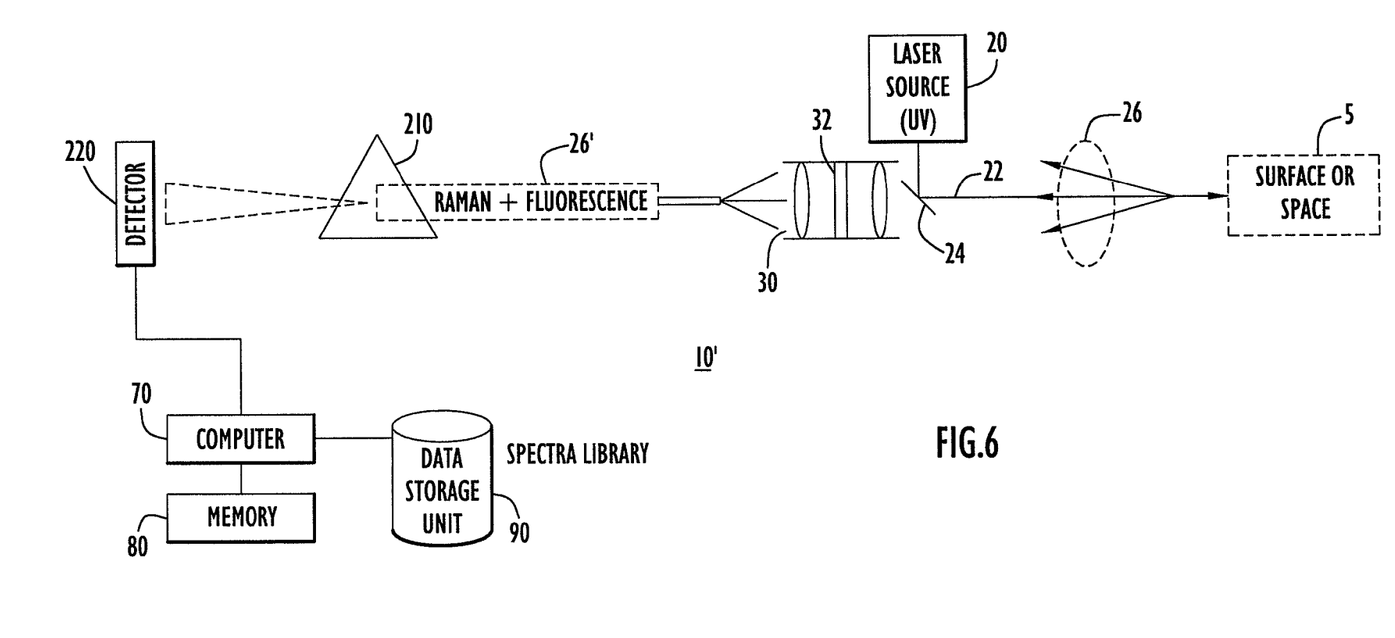
FIG. 6 is another example of a block diagram of a system for detecting the presence of a material of interest using Raman scattering and photofragmentation laser-induced fluorescence.

Turning no to FIG. 6, another example of a detection system is shown. The system 10' shown in FIG. 6 is similar to that shown in FIG. 1 except that it uses a single light dispersive element 210 instead of two light dispersive elements. The light dispersive element 210 disperses the combined Raman scattering and fluorescence to the detector 220. The detector 220 then converts the dispersed light to produce spectra that is supplied to the computer 70. The spectra produced may contain the full range of the Raman and full range of the LIF spectral windows, or only partial spectral features from the Raman spectra and from the LIF spectra. Although full range spectral windows of Raman scattering and LIF emissions may be collected, it may be desirable to use the non-overlapped regions in the analysis. The techniques described above in connection with FIGS. 2 and 3 may be employed in the system 100' to minimize interference when capturing the Raman scattering and the fluorescence.

Figure 7:
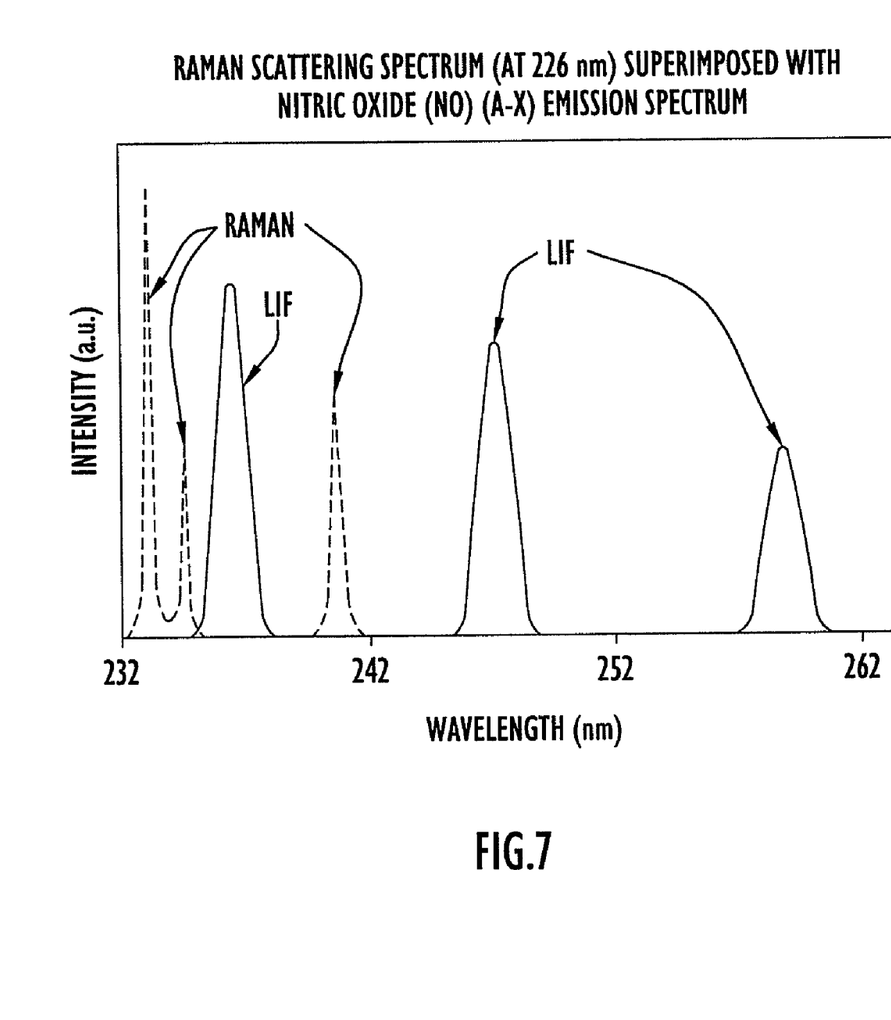
FIG. 7 illustrates an example of a plot for photofragment laser-induced fluorescence spectrum and a Raman spectrum according to another example where the material of interest is a nitro-based explosive material, and a detector configuration similar to that shown in FIG. 7 is used.

FIG. 7 illustrates an example of a plot of data that would be expected from the detector system configuration of FIG. 6 where a single dispersive element and single detector are used instead of dedicated elements/detectors for Raman and LIF.

Figure 8:
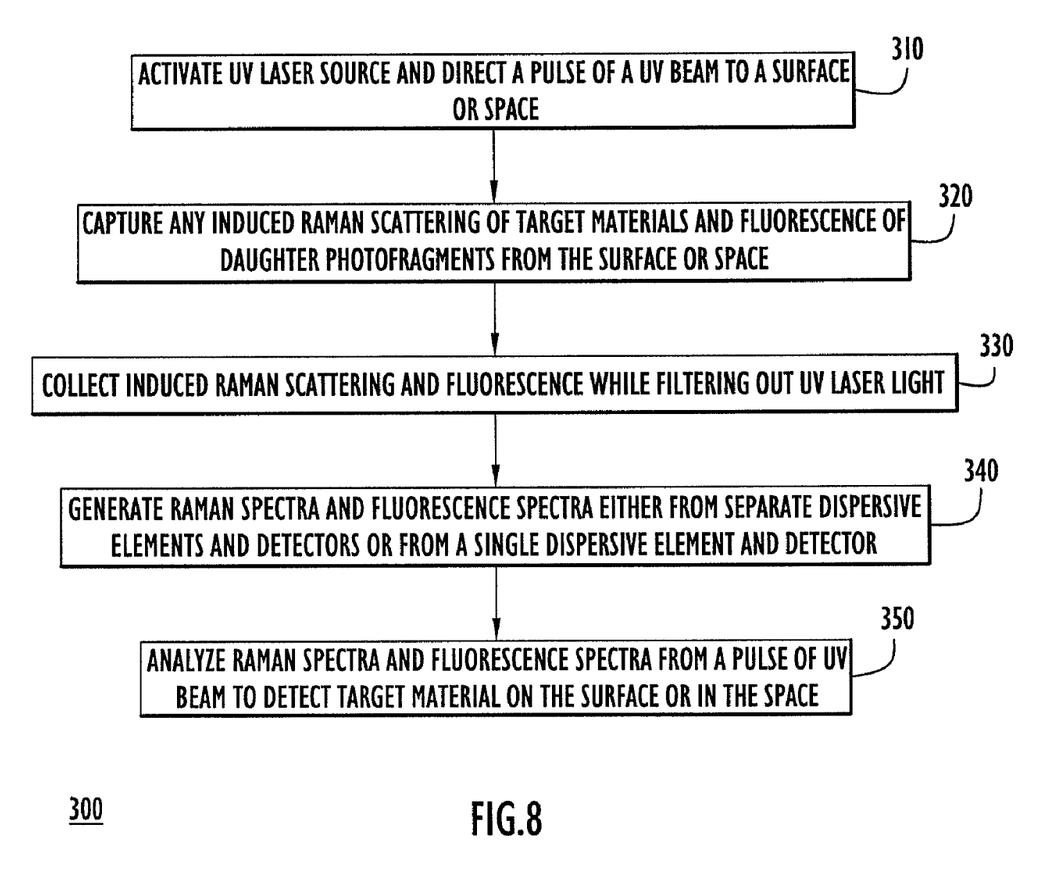
FIG. 8 illustrates an example of a flow chart depicting a process for detecting a material of interest based on Raman scattering and photofragmentation laser-induced fluorescence.

Reference is now made to FIG. 8 for a description of a detection process 300 that employs both Raman scattering and PF-LIF techniques. At 310, a UV laser source is activated to direct at least one pulse of a UV beam to a surface or space to be interrogated. In one embodiment, only a single pulse is directed to the surface of space, but in other embodiments a pulse of UV light at a first wavelength is emitted to achieve photodissociation and a pulse of UV light at a second wavelength is emitted to induce the fluorescence.

At 320, any induced Raman scattering and fluorescence is captured from the surface or space. At 330, the induced Raman scattering and fluorescence is collected and any light associated with the UV laser is filtered out. At 340, the Raman spectra and fluorescence spectra are generated after the collected light passes through either separate dispersive elements to separate detectors (as in the example of FIG. 1) or a single dispersive element to a single detector (as in the example of FIG. 6). At 350, the Raman spectra and fluorescence spectra are analyzed to detect presence of a material of interest on the surface or in the space.

There are numerous applications of the techniques described herein, including (without limitation) detection of explosive materials in solid, liquid or gas phase in any environment including a civilian environment (airports, mail, etc.) or battlefield environment, point detection of nitro-based or peroxide-based explosive materials at standoff distances with a hand-held or vehicle-mounted detector, detection of explosive materials in decontamination projects (pre- or post-explosion), and quantifying the amount or concentration of explosive materials from fluorescence intensity of photofragments. Other daughter fragments, such as CH, CC, CF, CN, NH, or NN, etc., if generated upon photodissociation of the target materials, may also be used to identify the respective parent target species. There may also be applications in which there are multiple daughter fragments (of a target material of interest) that fluoresce, but which one may have a more distinctive fluorescence spectra or a spectra in a region that is easier to analyze (does not overlap with a Raman spectra).

Although the apparatus, system, and method are illustrated and described herein as embodied in one or more specific examples, it is nevertheless not intended to be limited to the details shown, since various modifications and structural changes may be made therein without departing from the scope of the apparatus, system, and method and within the scope and range of equivalents of the claims. Accordingly, it is appropriate that the appended claims be construed broadly and in a manner consistent with the scope of the apparatus, system, and method, as set forth in the following claims.

What is claimed is:

1. A method comprising:
   directing a beam of ultraviolet light to a surface or space where a target material of interest may be present;
   capturing Raman scattering and fluorescence from the surface or space caused by the beam of ultraviolet light;
   generating Raman spectra and fluorescence spectra from the captured Raman scattering and fluorescence; and
   analyzing the fluorescence spectra and the Raman spectra to determine presence of the target material of interest on the surface or in the space when the Raman spectra indicates presence of a target species and the fluorescence spectra indicates presence of daughter photofragment molecules of the target species.

2. The method of claim 1, wherein capturing the fluorescence and generating the fluorescence spectra are performed a period of time after capturing the Raman scattering and generating the Raman spectra.

3. The method of claim 1, wherein determining comprises determining that a nitro-based explosive target material is present on the surface or in the space based on the fluorescence spectra and Raman spectra when the fluorescence spectra indicates fluorescence emitted by nitric oxide.

4. The method of claim 1, wherein determining comprises determining the presence a peroxide-based explosive target material on the surface or in the space based on the fluorescence spectra and Raman spectra when the fluorescence spectra indicates fluorescence emitted by hydroxyl radicals.

5. The method of claim 1, wherein determining comprises determining presence of an explosive target material on the surface or in the space based on the Raman spectra and the fluorescence spectra when the fluorescence spectra indicates fluorescence emitted by hydroxyl radicals.

6. The method of claim 1, wherein directing comprises directing a single pulse of the beam of ultraviolet light to the surface or space, and capturing, generating and analyzing are performed with respect to Raman scattering and fluorescence induced by said single pulse.

7. The method of claim 1, wherein directing comprises directing a pulse of the beam of ultraviolet light at a first wavelength to achieve photodissociation of the target species and a pulse of the beam of ultraviolet light at a second wavelength to induce the fluorescence of daughter photofragment molecules.

8. A system comprising:
   a light source that is configured to produce a beam of ultraviolet light directed to a surface or space where a target material of interest may be present;
   an optical element subsystem that is configured to capture Raman scattering and fluorescence from the surface or space that may be induced by the beam of ultraviolet light;
   at least one dispersive element that disperses the Raman scattering and the fluorescence;
   at least one detector that generates Raman spectra and fluorescence spectra from dispersed Raman scattering and fluorescence; and
   a computing unit that is configured to analyze the fluorescence spectra and the Raman spectra to determine presence of the target material of interest on the surface or in the space when the Raman spectra indicates presence of a target species and the fluorescence spectra indicates presence of daughter photofragment molecules of the target species.

9. The system of claim 8, and further comprising a first dispersive element configured to disperse the Raman scattering and a second dispersive element configured to disperse the fluorescence.

10. The system of claim 8, wherein the computing unit is configured to analyze the Raman spectra and fluorescence spectra induced by a single pulse of the beam of ultraviolet light.

11. The system of claim 8, wherein at least one detector generates the fluorescence spectra a period of time after with the Raman spectra.

12. The system of claim 8, wherein the computing unit is configured to analyze the Raman spectra and the fluorescence spectra to detect presence of a nitro-based explosive material as the target material based on the fluorescence spectra and Raman spectra when the fluorescence spectra indicates fluorescence emitted by nitric oxide.

13. The system of claim 8, wherein the computing unit is configured to analyze the Raman spectra and the fluorescence spectra, to detect presence of a peroxide-based explosive material as the target material based on the fluorescence spectra and Raman spectra when the fluorescence spectra indicates fluorescence emitted by hydroxyl radicals.

14. A method comprising:
    interrogating a surface or space with a beam of ultraviolet light;
    capturing Raman scattering and fluorescence caused by the beam of ultraviolet light;
    generating Raman spectra and fluorescence spectra from the captured Raman scattering and fluorescence; and
    analyzing the fluorescence spectra and the Raman spectra to determine presence of a target material of interest on the surface or in the space when the Raman spectra indicates presence of a target species and the fluorescence spectra indicates presence of daughter photofragment molecules of the target species.

15. The method of claim 14, wherein capturing the fluorescence and generating the fluorescence spectra are performed a period of time after capturing the Raman scattering and generating the Raman spectra.

16. The method of claim 14, wherein interrogating comprises directing a pulse of the beam of ultraviolet light at a first wavelength to achieve photodissociation of the target species and a pulse of the beam of ultraviolet light at a second wavelength to induce the fluorescence of daughter photofragment molecules.

17. The method of claim 14, wherein interrogating comprises directing a single pulse of the beam of ultraviolet light to the surface or space, and capturing, generating and analyzing are performed with respect to Raman scattering and fluorescence induced by said single pulse.

18. The method of claim 14, wherein analyzing comprises analyzing the Raman spectra and the fluorescence spectra to detect presence of an explosive target material when the fluorescence spectra is associated with fluorescence emitted by a daughter photofragment molecules produced by photodissociation of the explosive target material when irradiated with the beam of ultraviolet light.

19. The method of claim 2, wherein capturing the Raman scattering is performed after conclusion of a pulse of the beam of ultraviolet light to the surface or space.

20. The method of claim 15, wherein capturing the Raman scattering is performed after conclusion of a pulse of the beam of ultraviolet light to the surface or space.

* * * * *